(12) United States Patent
Locke

(10) Patent No.: US 12,097,093 B2
(45) Date of Patent: Sep. 24, 2024

(54) DRESSING BOLSTER WITH AREA PRESSURE INDICATOR

(71) Applicant: Solventum Intellectual Properties Company, Maplewood, MN (US)

(72) Inventor: Christopher Brian Locke, Bournemouth (GB)

(73) Assignee: Solventum Intellectual Properties Company, Maplewood, MN (US)

(*) Notice: Subject to any disclaimer, the term of this patent is extended or adjusted under 35 U.S.C. 154(b) by 744 days.

(21) Appl. No.: 17/045,868

(22) PCT Filed: Apr. 9, 2019

(86) PCT No.: PCT/US2019/026612
§ 371 (c)(1),
(2) Date: Oct. 7, 2020

(87) PCT Pub. No.: WO2019/199849
PCT Pub. Date: Oct. 17, 2019

(65) Prior Publication Data
US 2021/0137745 A1 May 13, 2021

Related U.S. Application Data

(60) Provisional application No. 62/657,341, filed on Apr. 13, 2018.

(51) Int. Cl.
*A61F 13/05* (2024.01)
*A61B 46/20* (2016.01)
(Continued)

(52) U.S. Cl.
CPC ............... *A61F 13/05* (2024.01); *A61B 46/20* (2016.02); *A61F 13/00059* (2013.01);
(Continued)

(58) Field of Classification Search
CPC ............... A61B 46/20; A61F 13/00029; A61F 13/00038; A61F 13/00068; A61F 13/0216;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

International Search Report and Written Opinion in International Application No. PCT/US2019/026612, mailed on Jul. 16, 2019.
(Continued)

*Primary Examiner* — Leslie A Lopez
*Assistant Examiner* — Jihad Dakkak

(57) ABSTRACT

A dressing for treating a tissue site with negative pressure may include a first layer configured to deform under a first predetermined negative pressure, and a second layer. The second layer may include an indicator configured to remain visible or hidden until the first layer deforms.

24 Claims, 5 Drawing Sheets

(51) Int. Cl.
*A61F 13/00* (2006.01)
*A61M 1/00* (2006.01)

(52) U.S. Cl.
CPC ............. *A61M 1/73* (2021.05); *A61M 1/732* (2021.05); *A61M 1/915* (2021.05); *A61M 1/966* (2021.05); *A61M 2205/6081* (2013.01)

(58) Field of Classification Search
CPC ..... A61F 13/0226; A61M 1/73; A61M 1/732; A61M 1/90; A61M 1/915; A61M 1/966; A61M 2205/6063; A61M 2205/6081
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 10,182,947 B2 * | 1/2019 | Hu ................ A61F 13/022 |
| 11,291,587 B2 * | 4/2022 | Kilpadi ............ A61F 13/00063 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2010/0022990 A1 | 1/2010 | Karpowicz et al. |
| 2010/0137775 A1* | 6/2010 | Hu ................ A61F 13/022 |
| | | 602/54 |
| 2011/0092927 A1* | 4/2011 | Wilkes ................ A61F 13/05 |
| | | 602/42 |
| 2012/0330252 A1* | 12/2012 | Stokes .................. G01L 1/24 |
| | | 604/318 |
| 2014/0005618 A1 | 1/2014 | Locke et al. |
| 2014/0180225 A1* | 6/2014 | Dunn .................. A61F 13/05 |
| | | 604/319 |
| 2015/0174304 A1* | 6/2015 | Askem ............ A61F 13/00042 |
| | | 604/319 |
| 2015/0283839 A1* | 10/2015 | Greener .............. B41M 5/1555 |
| | | 600/587 |
| 2017/0128272 A1 | 5/2017 | Wu et al. |
| 2017/0361045 A1 | 12/2017 | Fu et al. |
| 2019/0160845 A1* | 5/2019 | Greener ................ B41M 5/136 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |

(56) References Cited

FOREIGN PATENT DOCUMENTS

| | | |
|---|---|---|
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2007/030598 A2 | 3/2007 |
| WO | WO-2007/030601 A2 | 3/2007 |
| WO | WO-2009/093116 A1 | 7/2009 |
| WO | WO-2010/053870 A1 | 5/2010 |
| WO | WO-2014/140578 A1 | 9/2014 |
| WO | WO-2018/033794 A1 | 2/2018 |

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, . Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, "Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

* cited by examiner

DRESSING BOLSTER WITH AREA PRESSURE INDICATOR

CROSS-REFERENCE TO RELATED APPLICATIONS

This application claims the benefit of priority to international application PCT/US2019/026612, filed Apr. 9, 2019, and U.S. Provisional Application No. 62/657,341, filed on Apr. 13, 2018, the complete disclosures of which are hereby incorporated herein by reference in their entireties.

FIELD

The invention set forth in the appended claims relates generally to tissue treatment systems and more particularly, but without limitation, to systems and dressings for negative-pressure treatments that provide area pressure indication, and methods of using systems and dressings for negative-pressure treatment.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

SUMMARY

New and useful systems, apparatuses, and methods for treating tissue in a negative-pressure therapy environment and indicating area pressure in a negative-pressure therapy environment are set forth in the appended claims. Illustrative embodiments are also provided to enable a person skilled in the art to make and use the claimed subject matter.

For example, in some embodiments, a dressing for treating a tissue site with negative pressure may include a first layer configured to deform under a first predetermined negative pressure. A second layer may include an indicator configured to remain visible until the first layer deforms. The second layer may be configured to resist deformation under the first predetermined negative pressure.

In other embodiments, a dressing for treating a tissue site with negative pressure may comprise a first layer configured to deform under a first predetermined negative pressure, and a second layer. The second layer may comprise an indicator configured to remain hidden until the first layer deforms. The second layer may be configured to resist deformation under the first predetermined negative pressure.

In some embodiments, a system for treating a tissue site with negative pressure may include a negative-pressure source and a dressing. The dressing may comprise a first layer configured to deform under a first predetermined negative pressure, and a second layer. The second layer may comprise an indicator configured to remain hidden until the first layer deforms. The second layer may be configured to resist deformation under the first predetermined negative pressure.

Alternatively, in other embodiments, a dressing for treating a tissue site with negative pressure may comprise a top layer, a middle layer, and a bottom layer. The top layer may be configured to deform under a first predetermined negative pressure. The middle layer may be positioned adjacent the top layer and may comprise an indicator configured remain hidden until the first layer deforms. The middle layer may be configured to resist deformation under the first predetermined negative pressure. The bottom layer may be positioned adjacent the middle layer opposite the top layer and may be configured to deform under a second predetermined negative pressure that is less than the first predetermined negative pressure.

In other embodiments, a dressing for treating a tissue site with negative pressure may comprise a top layer, a middle layer, and a bottom layer. The top layer may be configured to deform under a first predetermined negative pressure. The middle layer may be positioned adjacent the top layer and may comprise an indicator configured remain visible until the first layer deforms. The middle layer may be configured to resist deformation under the first predetermined negative pressure. The bottom layer may be positioned adjacent the middle layer opposite the top layer and may be configured to deform under a second predetermined negative pressure that is less than the first predetermined negative pressure.

Advantageously, some embodiments of the dressings described herein may provide a visual indication of pressure along or within an entire area of the dressing. Other objectives, advantages, and a preferred mode of making and using the claimed subject matter may be understood best by reference to the accompanying drawings in conjunction with the following detailed description of illustrative embodiments.

DETAILED DESCRIPTION

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
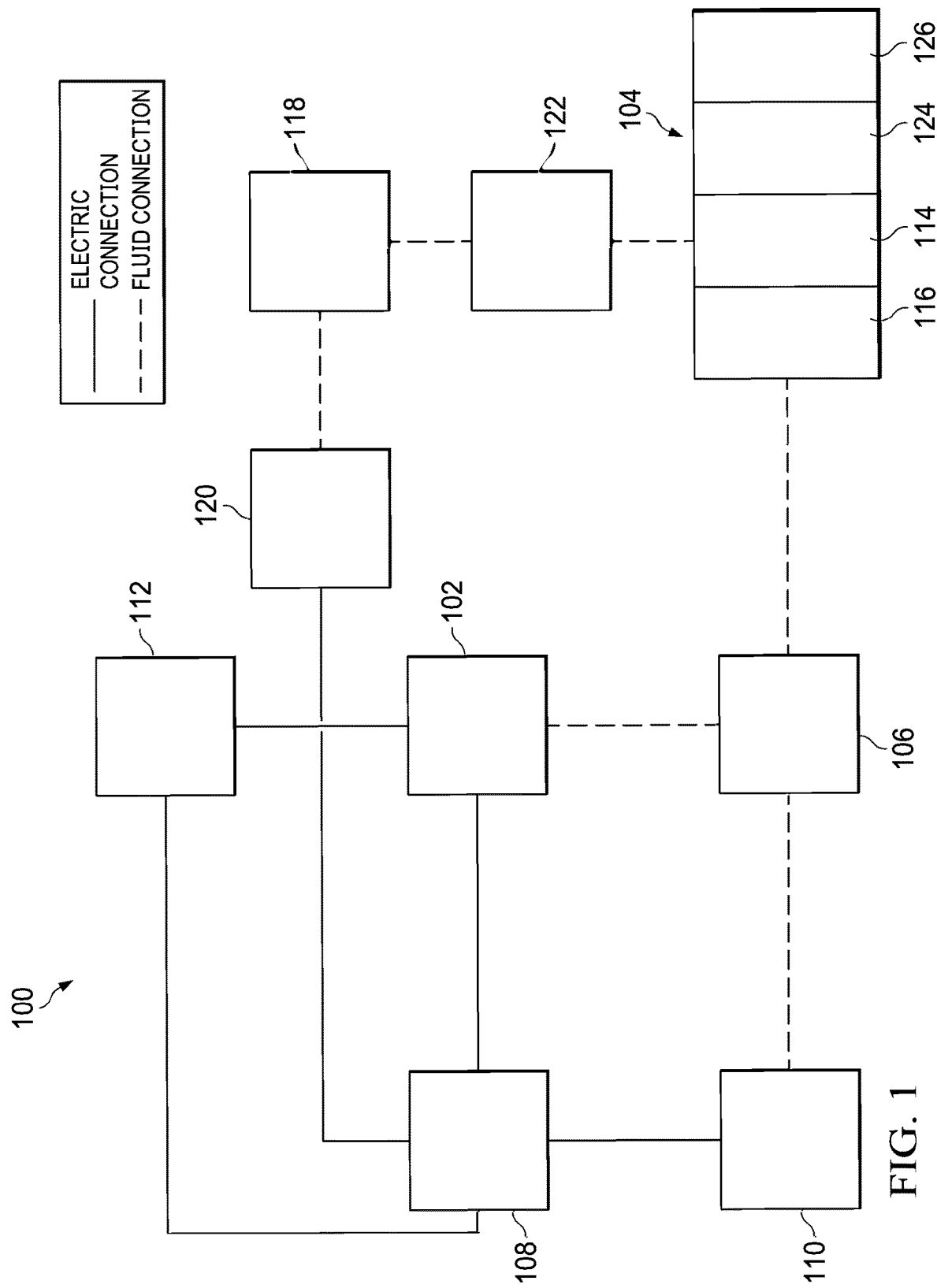
FIG. 1 is a functional block diagram of an example embodiment of a therapy system that can provide negative-pressure treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such as an injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include a source or supply of negative pressure, such as a negative-pressure source 102, a dressing 104, a fluid container, such as a container 106, and a regulator or controller, such as a controller 108, for example. Additionally, the therapy system 100 may include sensors to measure operating parameters and provide feedback signals to the controller 108 indicative of the operating parameters. As illustrated in FIG. 1, for example, the therapy system 100 may include a pressure sensor 110, an electric sensor 112, or both, coupled to the controller 108. In some embodiments, the dressing 104 may comprise or consist of one or more layers or components. For example, as illustrated in FIG. 1, the dressing 104 may comprise or consist essentially of a tissue interface 114, a cover 116, a pressure indicator 124, and a deformation layer 126.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 102 may be combined with the controller 108 and other components, shown by way of non-limiting example in FIG. 1 as components 118, 120, and 122, into a therapy unit.

In general, components of the therapy system 100 may be coupled directly or indirectly. For example, the negative-pressure source 102 may be directly coupled to the container 106, and may be indirectly coupled to the dressing 104 through the container 106. Coupling may include fluid, mechanical, thermal, electrical, or chemical coupling (such as a chemical bond), or some combination of coupling in some contexts. In some embodiments, components may also be coupled by virtue of physical proximity, being integral to a single structure, or being formed from the same piece of material. For example, the negative-pressure source 102 may be electrically coupled to the controller 108. The negative-pressure source 102 may be fluidly coupled to one or more distribution components, which provide a fluid path to a tissue site.

A distribution component is preferably detachable, and may be disposable, reusable, or recyclable. The dressing 104 and the container 106 are illustrative of distribution components. A fluid conductor is another illustrative example of a distribution component. A "fluid conductor," in this context, broadly includes a tube, pipe, hose, conduit, or other structure with one or more lumina adapted to convey a fluid between two ends. Typically, a tube is an elongated, cylindrical structure with some flexibility, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 104. For example, such a dressing interface may be a SENSAT.R.A.C.™ Pad available from KCI of San Antonio, Texas.

A negative-pressure supply, such as the negative-pressure source 102, may be a reservoir of air at a negative pressure, or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 106 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 108, may be a microprocessor or computer programmed to operate one or more components of the therapy system 100, such as the negative-pressure source 102. In some embodiments, for example, the controller 108 may be a microcontroller, which generally comprises an integrated circuit containing a processor core and a memory programmed to directly or indirectly control one or more operating parameters of the therapy system 100. Operating parameters may include the power applied to the negative-pressure source 102, the pressure generated by the negative-pressure source 102, or the pressure distributed to the tissue interface 114, for example. The controller 108 is also preferably configured to receive one or more input signals, such as a feedback signal, and programmed to modify one or more operating parameters based on the input signals.

Sensors, such as the pressure sensor 110 or the electric sensor 112, are generally known in the art as any apparatus operable to detect or measure a physical phenomenon or property, and generally provide a signal indicative of the phenomenon or property that is detected or measured. For example, the pressure sensor 110 and the electric sensor 112 may be configured to measure one or more operating parameters of the therapy system 100. In some embodiments, the pressure sensor 110 may be a transducer configured to measure pressure in a pneumatic pathway and convert the measurement to a signal indicative of the pressure measured. In some embodiments, for example, the pressure sensor 110 may be a piezoresistive strain gauge. The electric sensor 112 may optionally measure operating parameters of the negative-pressure source 102, such as the voltage or current, in some embodiments. Preferably, the signals from the pressure sensor 110 and the electric sensor 112 are suitable as an input signal to the controller 108, but some signal conditioning may be appropriate in some embodiments. For example, the signal may need to be filtered or amplified before it can be processed by the controller 108. Typically, the signal is an electrical signal, but may be represented in other forms, such as an optical signal.

The tissue interface 114 can be generally adapted to contact a tissue site. The tissue interface 114 may be partially or fully in contact with the tissue site. If the tissue site is a wound, for example, the tissue interface 114 may partially or completely fill the wound, or may be placed over the wound. The tissue interface 114 may take many forms, and may have many sizes, shapes, or thicknesses depending on a variety of factors, such as the type of treatment being implemented or the nature and size of a tissue site. For example, the size and shape of the tissue interface 114 may be adapted to the contours of deep and irregular shaped tissue sites. Moreover, any or all of the surfaces of the tissue interface 114 may have projections or an uneven, course, or jagged profile that can induce strains and stresses on a tissue site, which can promote granulation at the tissue site.

In some embodiments, the tissue interface 114 may comprise or consist essentially of a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some illustrative embodiments, the pathways of a manifold may be interconnected to improve distribution or collection of fluids across a tissue site. Additionally, or alternatively, the fluid path may be reversed or a secondary fluid path may be provided in some embodiments to facilitate delivering fluid such as from a source of instillation solution across a tissue site.

In some embodiments, the cover 116 may provide a bacterial barrier and protection from physical trauma. The cover 116 may also be constructed from a material that can reduce evaporative losses and provide a fluid seal between two components or two environments, such as between a therapeutic environment and a local external environment. The cover 116 may be, for example, an elastomeric film or membrane that can provide a seal adequate to maintain a negative pressure at a tissue site for a given negative-pressure source. The cover 116 may have a high moisture-vapor transmission rate (MVTR) in some applications. For example, the MVTR may be at least 300 g/m^2 per twenty-four hours in some embodiments. In some example embodiments, the cover 116 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

In general, the pressure indicator 124 may provide a means for indicating pressure changes and may be fluidly coupled to a side of the tissue interface 114, such that the means for indicating pressure is between the tissue interface and the cover 116. In some embodiments, the deformation layer 126 may be coupled to a side of the pressure indicator 124 opposite the tissue interface 114. The deformation layer 126 is configured to deform under a first predetermined negative pressure. The pressure indicator 124 is configured to remain visible until the deformation layer 126 deforms. The pressure indicator 124 is configured to resist deformation under the first predetermined negative pressure.

An attachment device may be used to attach the cover 116 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 116 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

Figure 2:
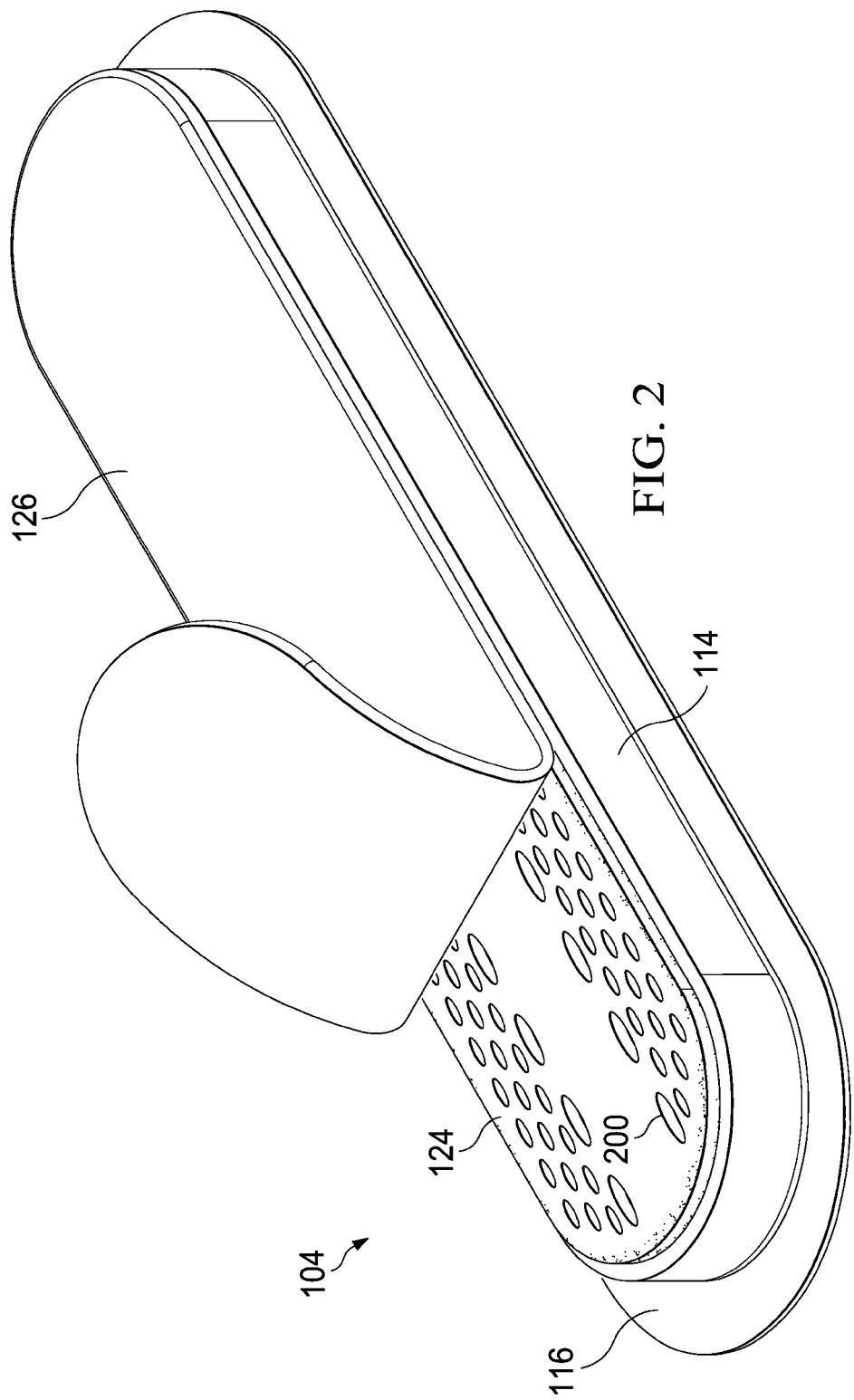
FIG. 2 is a schematic, partial assembly view of an example of a dressing for use with the therapy system of FIG. 1.

FIG. 2 is a schematic, partial assembly view of an example of the dressing 104, illustrating additional details that may be associated with some embodiments. In the example of FIG. 2, the dressing 104 comprises the deformation layer 126, the pressure indicator 124, and the tissue interface 114. The pressure indicator 124 may be an indicator layer between the deformation layer 126 and the tissue interface 114.

In the example of FIG. 2, the tissue interface 114 is a manifold, which may comprise or consist essentially of open-cell foam, a porous tissue collection, or other porous material such as gauze or felted mat generally include pores, edges, and/or walls adapted to form interconnected fluid channels. Liquids, gels, and other foams may also include or be cured to include apertures and fluid pathways suitable for the tissue interface 114 of FIG. 2. In some embodiments, the tissue interface 114 may additionally or alternatively comprise projections that form interconnected fluid pathways. For example, the tissue interface 114 may be molded to provide surface projections that define interconnected fluid pathways.

The average pore size of foam may vary according to needs of a prescribed therapy. For example, in some embodiments, the tissue interface 114 may comprise or consist essentially of foam having pore sizes in a range of 400-600 microns. The tensile strength of the tissue interface 114 may also vary according to needs of a prescribed therapy. For example, the tensile strength of foam may be increased for instillation of topical treatment solutions. In one non-limiting example, the tissue interface 114 may be a reticulated polyurethane foam such as GRANUFOAM™ dressing or V.A.C. VERAFLO™ dressing, both available from KCI of San Antonio, Texas.

The tissue interface 114 may be either hydrophobic or hydrophilic. In an example in which the tissue interface 114 may be hydrophilic, the tissue interface 114 may also wick fluid away from a tissue site, while continuing to distribute negative pressure to the tissue site. The wicking properties of the tissue interface 114 may draw fluid away from a tissue site by capillary flow or other wicking mechanisms. An example of a hydrophilic foam is a polyvinyl alcohol, open-cell foam such as V.A.C. WHITEFOAM™ dressing available from KCI of San Antonio, Texas. Other hydrophilic foams may include those made from polyether. Other foams that may exhibit hydrophilic characteristics include hydrophobic foams that have been treated or coated to provide hydrophilicity.

The tissue interface 114 may further promote granulation at a tissue site when pressure within the sealed therapeutic environment is reduced. For example, any or all of the surfaces of the tissue interface 114 may have an uneven, coarse, or jagged profile that can induce microstrains and stresses at a tissue site if negative pressure is applied through the tissue interface 114.

In some embodiments, the tissue interface 114 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 114 may further serve as a scaffold for new cell-growth, or a scaffold material may be used in conjunction with the tissue interface 114 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The tissue interface 114 of FIG. 2 generally has a first planar surface and a second planar surface opposite the first planar surface. The thickness of the tissue interface 114 between the first planar surface and the second planar surface may also vary according to needs of a prescribed therapy. For example, the thickness of the tissue interface 114 may be decreased to relieve stress on other layers and to reduce tension on peripheral tissue. The thickness of the tissue interface 114 can also affect the conformability of the tissue interface 114. In some embodiments, a thickness in a range of about 5 millimeters to 10 millimeters may be suitable.

In some embodiments, the deformation layer 126 is spaced apart from the tissue interface 114. The deformation layer 126 may be formed of felted foam or other open-celled/reticulated polyurethane or other perforated closed-celled foam. The deformation layer 126 should be sufficiently stiff that the deformation layer 126 only deforms at therapeutic ranges of negative pressure. For example, the deformation layer 126 may deform at a pressure of about 125 mmHg.

A thickness of the deformation layer 126 may range from about 4 mm to about 8 mm (e.g., about 5 mm to about 7 mm or about 5.5 mm to about 6.5 mm). The thickness of the deformation layer 126 may be adjusted and matched to a modulus of the material so as to attain appropriate deformation. The thickness of the deformation layer 126 should be as thin as possible such that the deformation layer 126 does not adversely affect lateral contraction of the dressing 104.

In some embodiments, the deformation layer 126 includes a plurality of perforations, such as oval perforations. Perforations can facilitate matching the lateral contraction of the deformation layer 126 to other layers of the dressing 104 without impacting vertical compression of the deformation layer 126.

The deformation layer 126 can have a same color as a color of the tissue interface 114.

The pressure indicator 124 can be between the tissue interface 114 and the deformation layer 126. The pressure indicator 124 can be formed of felted foam or other open-celled/reticulated polyurethane material or other foam that is sufficiently stiff, such that the pressure indicator 124 will not substantially compress before the deformation layer 126 deforms. The material used to form the pressure indicator 124 can be the same material as the deformation layer 126. In some embodiments, the material used to form the pressure indicator 124 is a layer of reticulated foam. In some embodiment, the pressure indicator 124 may be thicker than the deformation layer 126.

In some embodiments, the pressure indicator 124 includes perforations 200 that can be formed by removing material from the pressure indicator 124. The perforations 200 can assist the pressure indicator 124 in readily collapsing once sufficient pressure is applied.

The pressure indicator 124 of FIG. 2 may have a smaller footprint than the deformation layer 126 and the tissue interface 114. For example, the pressure indicator 124 can have dimensions that are about 2 mm to about 5 mm smaller than dimensions of the deformation layer 126 and the tissue interface 114. The pressure indicator 124 is visible from a side of the dressing 104 prior to application of pressure. In other embodiments, the pressure indicator 124 may comprise a circumferential perimeter having a greater length than a length of a circumferential perimeter of the deformation layer 126 forming a margin on a surface of the pressure indicator 124.

Preferably, the pressure indicator 124 is a different color than the deformation layer 126 and/or includes a distinctive symbol on at least a portion of the pressure indicator 124. The pressure indicator 124 is visible until the deformation layer 126 deforms and covers the pressure indicator 124 so as to provide visible indication that therapeutic pressure has been applied to an area.

Figure 3:
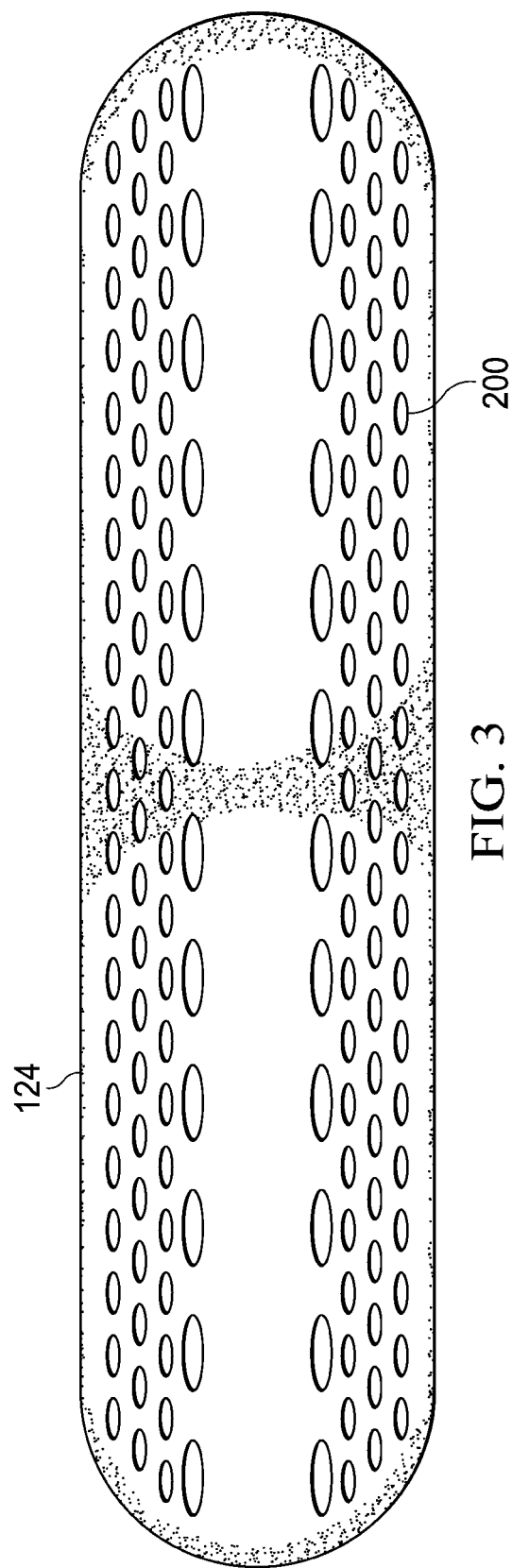
FIG. 3 is a schematic, top view of an indicator layer of the dressing of FIG. 2.

FIG. 3 is a schematic, top view of the pressure indicator 124 illustrating additional details that can be associated with some embodiments. In some embodiments, the pressure indicator 124 includes the perforations 200 along at least a portion of the pressure indicator 124. The perforations 200 can vary in size. For example, in some embodiments, the pressure indicator 124 includes a plurality of rows of perforations 200. A first row can have smaller perforations 200 than a second row. The perforations 200 can be uniformly formed across the pressure indicator 124. In other embodiments, the perforations 200 are non-uniformly formed in the pressure indicator 124. A central portion of the pressure indicator 124 can not include any of the perforations 200, while edge portions of the pressure indicator 124 include the perforations 200.

Figure 4:
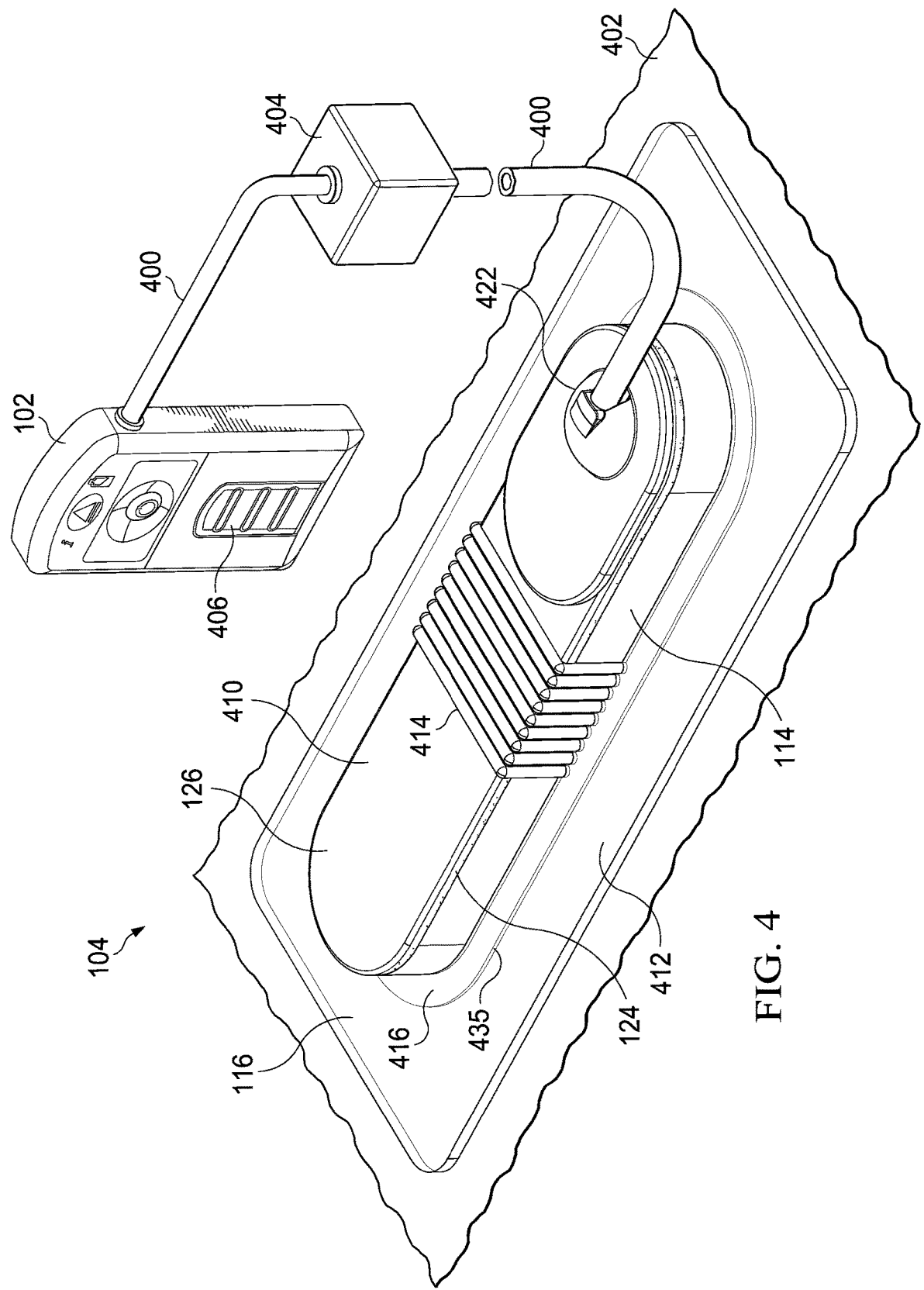
FIG. 4 is a schematic, perspective view of a dressing including a pressure indicator that may be associated with some embodiments of the therapy system of FIG. 1.

FIG. 4 is a schematic, perspective view of an example of the therapy system 100 of FIG. 1, illustrating additional details that may be associated with some embodiments. In the example of FIG. 4, the negative-pressure source 102 may be a portable vacuum pump, which can be manually-actuated or powered by batteries in some embodiments. In the example embodiment of FIG. 4, the dressing 104 generally includes the pressure indicator 124, the tissue interface 114, the deformation layer 126, and the cover 116.

In some embodiments, as shown in FIG. 4, the therapy system can include one or more fluid conductors, such as tubing 400, and a dressing interface 422. As shown in the example of FIG. 4, the tubing 400 may include a flexible tube, which can be fluidly coupled on one end to the dressing interface 422. In some embodiments, the dressing interface 422 may be an elbow connector. The negative-pressure source 102 may be in fluid communication with the dressing interface 422 via the tubing 400.

In some embodiments, as shown in FIG. 4, a container 406 may be integral with or mechanically coupled to the negative-pressure source 102. One or more containment devices, such as a representative containment device 404, may be fluidly coupled to the tubing 400. The containment device 404 may be, for example, another fluid reservoir, or collection member to hold exudates and other fluids removed, a pressure-feedback device, a volume detection system, a blood detection system, an infection detection system, a flow monitoring system, a temperature monitoring system, etc. Multiple containment devices 404 may be included. Some of the containment devices 404 may be formed integrally to the negative-pressure source 102.

In some embodiments, as shown in FIG. 4, the cover 116 provides a fluid seal over the dressing 104 and at least a portion of a patient's epidermis 402. The cover 116 may be sealed against the epidermis 402 or against a gasket or drape by an attachment device, such as a pressure-sensitive adhesive 435.

The cover 116 can include a first cover portion 410 and a second cover portion 412. The first cover portion 410 extends over a first side of the dressing 104 and extends further to form a cover extension, such as a flange 416. An aperture may be formed on a portion of the cover 116 to allow fluid communication with the dressing interface 422.

The flange 416 may be placed on a top side of the second cover portion 412 and coupled, such as by an adhesive, bond, welding (e.g., ultrasonic or RF welding), cements, etc. Alternatively, the first cover portion 410 and second cover portion 412 can be integrally formed. The first cover portion 410 can include a plurality of bellows 414, folds, or stretch zones. The bellows 414 allow additional cover material to become available, to stretch, or to move, if needed. For example, if the dressing 104 is used on a joint, when the joint is flexed, additional drape material may be necessary or movement necessary and this will be facilitated by the bellows 414.

One or more release members (not shown) may be releasably coupled to the first side of the second cover portion 412. The release members provide stiffness and help during deployment of the dressing 104. The release members are typically either casting paper or a film held on the first side of the second cover portion 412.

Figure 5A:
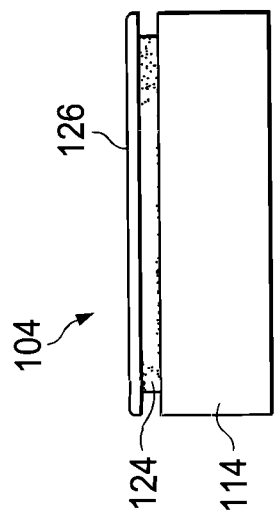
FIGS. 5A, 5B, and 5C are schematic end views of a dressing that may be associated with an example embodiment of therapy system of FIG. 1.
Figure 5B:
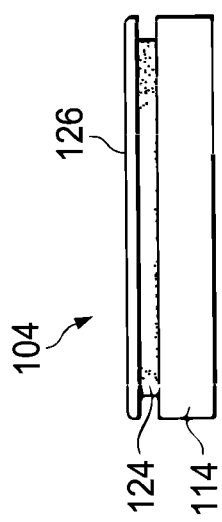
Figure 5C:
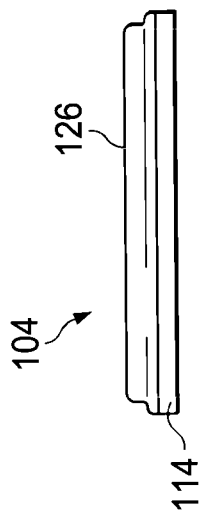

FIGS. 5A, 5B, and 5B are schematic end views of an example of the dressing 104, illustrating additional details that may be associated with some embodiments. In some embodiments, as shown in FIG. 5A, if the dressing 104 is applied to a tissue site without negative pressure, the pressure indicator 124 remains visible when viewed from a side. As shown in FIG. 5B, if negative pressure less than a therapeutic level is applied to the dressing, the pressure indicator 124 remains visible so as to indicate that therapeutic pressure has not been reached. For example, the tissue interface 114 may compress at about 50 mmHg, while the pressure indicator 124 and the deformation layer 126 remain uncompressed at 50 mmHg. As shown in FIG. 5C, if a therapeutic level of negative pressure is applied to the dressing 104, the deformation layer 126 deforms such that the pressure indicator 124 cannot be seen from a side of the dressing 104, indicating that adequate therapeutic pressure has been applied to the dressing 104.

In an alternative embodiment, the dressing 104 may be configured such that the pressure indicator 124 is not visible from a side of the dressing 104 until negative-pressure is applied and the deformation layer 126 contracts. In this embodiment, the pressure indicator 124 may have larger dimensions than the deformation layer 126. For example, the pressure indicator 124 may have about a same circumference or larger than a circumference the tissue interface 114 and the deformation layer 126. The pressure indicator 124 could be any color that is different than a color of the tissue interface 114 and the deformation layer 126. In some embodiments, the pressure indicator may include a distinctive symbol that only becomes visible when negative-pressure is applied. The deformation layer 126 may include perforations to permit gross lateral contraction, such that movement of the deformation layer 126 exposes the colored pressure indicator 124 or the symbol to indicate that therapeutic pressure has been delivered.

In other embodiments, the layers of the dressing 104 may be reordered and the dressing 104 may include additional layers.

In some embodiments, the tissue interface 114 may be thinned so that the pressure indicator 124 is closer to a tissue surface. In other embodiments, the dressing 104 could include chambers within the dressing 104, such that collapse is driven from the bottom of the dressing 104 up, rather than from the top of the dressing down.

The systems, apparatuses, and methods described herein may provide significant advantages. For example, since the pressure indicator 124 is over a large portion or all of the dressing 104, the pressure is indicated over substantially all of the dressing 104. For instance, if there is a blockage or restriction within the tissue interface 114 due to viscose exudates, the pressure indicator 124 can indicate that uniform pressure is not being delivered over the area of the dressing 104. The pressure indicator 124 may be combined with other dressings which may be used over areas, such as a range of other post-operative wounds, grafts, etc.

Additionally, or alternatively, the dressing 104 described herein can provide a visual indication of the application of a prescribed therapeutic pressure over an entire dressing. The pressure indicator 124 may also provide visible identification of one or more locations of fluid restriction within the dressing 104.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context.

Features, elements, and aspects described in the context of some embodiments may also be omitted, combined, or replaced by alternative features serving the same, equivalent, or similar purpose without departing from the scope of the invention defined by the appended claims. For example, one or more of the features of some layers may be combined with features of other layers to provide an equivalent function.

Components may also be combined or eliminated in various configurations for purposes of sale, manufacture, assembly, or use. For example, in some configurations the dressing 104, the container 106, or both may be eliminated or separated from other components for manufacture or sale. In other example configurations, components of the dressing 104 may also be manufactured, configured, assembled, or sold independently or as a kit.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. A dressing for treating a tissue site with negative pressure, the dressing comprising:
    a first layer configured to deform under a first predetermined negative pressure; and
    a second layer comprising an indicator configured to remain visible until the first layer deforms and to not be visible after the first layer deforms, wherein the second layer is configured to resist deformation under the first predetermined negative pressure, and wherein the indicator comprises at least one of a distinctive color or a symbol that does not change and is different from at least the first layer.

2. The dressing of claim 1, wherein
    the second layer comprises a first surface that is configured to face away from the tissue site and a second surface that is configured to face toward the tissue site;
    the first layer is adjacent the first surface; and
    the second layer is configured to be positioned between the tissue site and the first layer.

3. The dressing of claim 2, wherein the indicator is located on a portion of the first surface of the second layer.

4. The dressing of claim 1, wherein the first layer is configured to cover the indicator when the first layer deforms.

5. The dressing of claim 1, wherein the indicator is located on an edge surface of the second layer.

6. The dressing of claim 1, wherein the second layer comprises a circumferential perimeter having a greater length than a length of a circumferential perimeter of the first layer forming a margin on a surface of the second layer.

7. The dressing of claim 6, wherein the indicator is positioned on the margin.

8. The dressing of claim 1, wherein:
    the second layer comprises a first surface that is configured to face away from the tissue site and a second surface that is configured to face toward the tissue site; and
    the first layer is adjacent the second surface.

9. The dressing of claim 8, wherein the indicator is located on a portion of a surface of the first layer.

10. The dressing of claim 8, wherein the second layer is configured to cover the indicator when the first layer deforms.

11. The dressing of claim 1, further comprising a third layer configured to deform under a second predetermined negative pressure that is less than the first predetermined negative pressure.

12. The dressing of claim 11, wherein
    the second layer comprises a first surface that is configured to face away from the tissue site and a second surface that is configured to face toward the tissue site;
    the first layer is adjacent the first surface; and
    the third layer is adjacent the second surface.

13. The dressing of claim 1, wherein the first layer comprises at least one of felted foam, open-celled foam, or perforated closed-celled foam.

14. The dressing of claim 1, wherein the first layer comprises perforations configured to allow the first layer to deform under the first predetermined negative pressure.

15. The dressing of claim 1, further comprising:
    a drape configured to form a sealed space over the tissue site, wherein the first layer and the second layer are configured to be positioned in the sealed space;
    an aperture in the drape; and
    an interface comprising:
        a base coupled to the drape around the aperture, and
        a fluid port coupled to the base and configured to provide fluid communication through the drape.

16. A dressing for treating a tissue site with negative pressure, the dressing comprising:
    a top layer configured to deform under a first predetermined negative pressure;
    a middle layer positioned adjacent the top layer and comprising an indicator that does not change and is configured to remain visible until the top layer deforms and to not be visible after the top layer deforms under the first predetermined negative pressure, wherein the middle layer is configured to resist deformation under the first predetermined negative pressure; and a bottom layer positioned adjacent the middle layer opposite the top layer and configured to deform under a second predetermined negative pressure that is less than the first predetermined negative pressure.

17. The dressing of claim 16, wherein the middle layer comprises a circumferential perimeter having a greater length than a length of a circumferential perimeter of the top layer forming a margin on a surface of the middle layer.

18. The dressing of claim 16, wherein:

the middle layer comprises a first surface that is configured to face away from the tissue site and a second surface that is configured to face toward the tissue site;

the top layer is adjacent the first surface; and the bottom layer is adjacent the second surface.

19. A dressing for treating a tissue site with negative pressure, the dressing comprising:

a deformation layer configured to deform under a first predetermined negative pressure; and an indicator layer configured to identify one or more locations of a fluid restriction within the dressing, wherein the indicator layer is configured to resist deformation under the first predetermined negative pressure, and wherein the indicator layer comprises at least one of a distinctive color or a symbol that does not change and is not visible after the deformation layer deforms in a location of the dressing that has reached the first predetermined negative pressure.

20. The dressing of claim 19, wherein:

the indicator layer comprises a first surface that is configured to face away from the tissue site and a second surface that is configured to face toward the tissue site; and the deformation layer is adjacent the first surface.

21. The dressing of claim 19, wherein the deformation layer is configured to cover one or more portions of the indicator layer when the deformation layer deforms; and the one or more locations of the fluid restriction within the dressing correspond with one or more locations that have not reached the first predetermined negative pressure where the indicator layer remains visible.

22. The dressing of claim 19, wherein the distinctive color or symbol is located on a surface of the indicator layer.

23. The dressing of claim 19, wherein the indicator layer comprises a circumferential perimeter having a greater length than a length of a circumferential perimeter of the deformation layer forming a margin on a surface of the indicator layer.

24. The dressing of claim 19, further comprising:

a drape configured to form a sealed space over the tissue site, wherein the deformation layer and the indicator layer are configured to be positioned in the sealed space;

an aperture in the drape; and an interface comprising:

a base coupled to the drape around the aperture, and a fluid port coupled to the base and configured to provide fluid communication through the drape.

* * * * *